United States Patent [19]

Gaitanopoulos et al.

[11] 4,405,787

[45] Sep. 20, 1983

[54] 3-CARBOXY-2-AZABICYCLO[2.2.1]HEPTANE DERIVATIVES

[75] Inventors: Dimitri Gaitanopoulos, Eagleville; Joseph Weinstock, Phoenixville, both of Pa.

[73] Assignee: SmithKline Beckman Corporation, Philadelphia, Pa.

[21] Appl. No.: 365,139

[22] Filed: Apr. 5, 1982

[51] Int. Cl.³ ............................................. C07D 487/00
[52] U.S. Cl. ...................................................... 546/112
[58] Field of Search .......................................... 546/112

[56] References Cited

PUBLICATIONS

M. S. Raasch, J. Org. Chem., 40 161 (1979).

A. J. G. Baxter et al., J. Chem. Soc. Perkins I, 2343 (1977).
G. R. Krow et al., Tetrahedron Letters, 23 1971 (1978).
J. M. Biehler et al., Tetrahedron, 3171 (1971).
M. E. Jung et al., Tetrahedron Letters, 22 4607 (1981).

*Primary Examiner*—Henry R. Jiles
*Assistant Examiner*—Bernard Dentz
*Attorney, Agent, or Firm*—William H. Edgerton; Richard D. Foggio; Alan D. Lourie

[57] ABSTRACT

3-Carboxy-2-(ω-carboxyalkanoyl)-2-azabicyclo-[2.2.1]heptenes have been demonstrated to improve kidney function. 3-Carboxy-2-azabicyclo[2.2.1]heptane and its esters are important new chemical intermediates.

10 Claims, No Drawings

3-CARBOXY-2-AZABICYCLO[2.2.1]HEPTANE DERIVATIVES

This invention relates to a new series of heterocyclic amino acid containing compounds. More specifically, this invention relates to 3-carboxy-2-(ω-carboxyalkanoyl)-2-azabicyclo[2.2.1]heptanes and intermediates for preparing them.

BACKGROUND OF THE INVENTION

As far as we are aware, no chemical compounds which have a 3-carboxy-2-azabicyclo[2.2.1]heptane nucleus have been previously reported to have any biological activity.

Most of the related compounds described in the prior art were prepared to study certain chemical reactions, especially, the Diels-Alder addition reaction used to form such cyclic compounds.

For example, M. S. Roasch, J. Org. Chem. 40 161 (1979), describes the use of 2-(p-toluenesulfonyl)-2-azabicyclo[2.2.1]hept-5-ene-exo-3-carboxylic acid. This compound has a double bond in the azabicycloheptane ring and a difficulty removable tosyl group at the N-ring member. A. J. G. Baxter et al., J. Chem. Soc. Perkins I, 2343 (1977), describes the preparation of azabicyclo[2.2.2]octenes using the Diels-Alder reaction with an iminoacetate and cyclohexadiene. G. R. Krow et al., Tetrahedron Letters 23 1971 (1978), describes the similar preparation of 3-carbethoxy-2-carbobenzyloxy-2-azabicyclo-[2.2.2]oct-5-enes.

J. M. Biehler et al., Tetrahedron, 3171 (1971), describes certain 2-azabicyclo[2.2.1]heptanes which have two carboxylic acid functions, such as cyano or carboxamido, at the 3-position. M. E. Jung et al., Tetrahedron Letters 22 4607 (1981), discloses the preparation of a number of 2-carboalkoxy-3-carbethoxy-2-azabicyclo[2.2.1]heptenes. This publication was received in the United States on Nov. 19, 1981, well after our reduction-to-practice of the invention described hereafter.

DESCRIPTION OF THE INVENTION

The compounds of this invention are represented by the following structural formula:

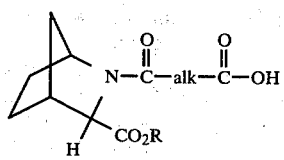

I in which:
R is hydrogen, lower alkyl of 1–5 carbons or benzyl; and
alk is an alkylene chain of from 2–5 carbons separating the carboxy and carboxamido groups to which it is attached by at least 2, but, preferably, at least 3, carbons.

A preferred group of compounds are those of formula I in which alk is propylene (—CH$_2$CH$_2$CH$_2$—) or α-methylpropylene

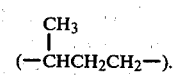

Also, R is, preferably, hydrogen.

Included along with the compounds of formula I are the nontoxic, pharmaceutically acceptable salts of the azabicyclic carboxylic acids having nontoxic alkali metal or organic amine cations. Exemplary of such salts are those having sodium, potassium, calcium, cyclohexylamine, butylamine, ethylamine or ethylenediamine cations. The salts are prepared by reacting the heterocyclic acid with one or two equivalents of the chosen base in a suitable organic solvent such as aqueous alcohol or by similar chemical methods known to the art.

The compounds of this invention have been found to have a pharmacodynamic activity which is especially useful in improving kidney function. For example, the compound of formula I in which R is hydrogen and alk is propylene is a water diuretic as well as a natruretic in the spontaneously hypertensive rat model at 50 mg/kg of test compound when administered intraperitoneally. The compound of formula I in whose structure R is hydrogen and alk is α-methylpropylene, at 3 μg/kg/min infusion in two anesthetized dogs, increased renal blood flow and decreased renal vascular resistance significantly. Dopamine, in this protocol, also increases blood flow and decreases resistance.

The compounds of this invention, therefore, have utility as active ingredients formulated in pharmaceutical dosage units, as well as in methods, for improving renal function in patients in need thereof. These methods comprise administering to the patient an effective, nontoxic quantity of the active ingredient, either orally or, preferably, parenterally. The active ingredient will be incorporated into dosage units using standard methods utilizing from 100–500 mg of compound measured as the free acid. The dosage units are then administered from 2–5 times daily orally. An equivalent quantity is administered parenterally, such as by infusion or subcutaneous injection.

The compounds of formula I are prepared by the following reaction sequence:

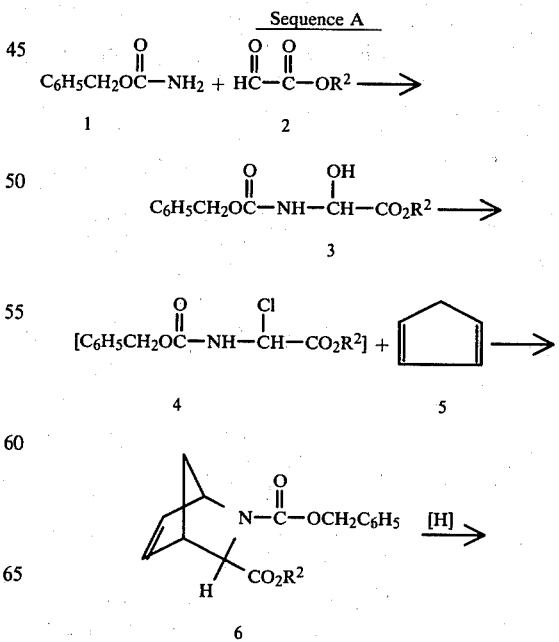

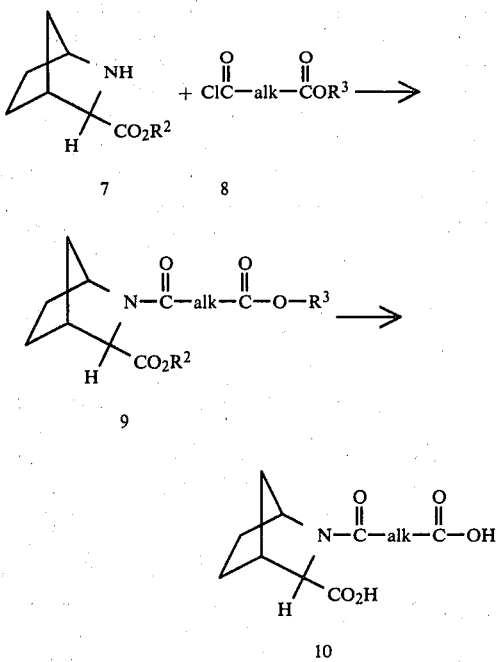

-continued
Sequence A 7   8

9

10

In reaction sequence A, alk is as defined above, $R^2$ is lower alkyl of 1–5 carbons or benzyl and $R^3$ is benzyl or a similar protective group, which is easily removed by hydrogenation or mild hydrolysis, including allyl or haloalkyl groups.

One of the key reactions of this synthetic sequence is the Diels-Alder reaction of cyclopentadiene (5) with an imine. The imine is generated, usually in situ, from a 2-chloro-N-carbalkoxyglycinate (4) by dehydrohalogenation using a tertiary organic amine such as triethylamine. The Diels-Alder reaction is carried out in a suitable organic solvent, such as methylene chloride, in the cold initially and, then, at room temperature overnight. The resulting product is the 2-carboalkoxy-3-carboalkoxy-2-azabicyclo[2.2.1]hept-5-ene (7). This compound is, conveniently, hydrogenated under low pressure using a noble metal catalyst, such as palladium, to remove the protective group at position 2 and reduce the ring unsaturation in one chemical step.

The resulting compound, 7, and its derivatives are important intermediates which can be used to prepare a number of biologically active end products, including the compounds described above. The acid form of this heterocyclic amino acid is easily prepared from its esters by hydrolysis using alcoholic alkali. These intermediates, which are also part of this invention, are represented by the following formula:

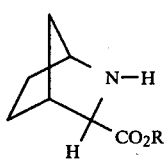

II in which R is hydrogen, $C_{1-5}$ lower alkyl or benzyl.

Also included in this invention are acid addition salts, together with alkali or organic amine salts, of the heterocyclic amino acids of formula II which can equivalently be used for general synthetic purposes.

The 2-azabicyclo[2.2.1]heptane intermediates (7), with either a carboxy or a carboalkoxy group at position 3, are then reacted with one equivalent of a ω-carboalkoxyalkanoyl chloride or bromide (8) in the presence of an organic or inorganic base in a suitable solvent system in the cold to give the desired end products in the ester prodrug form (9). Good yields were obtained using a solvent system of triethylamine in acetone at from 0°–25°. Other reactive mixed ester groups or anhydrides may be used instead of the half acid halides. The protective ω-ester groups are then optionally split, such as by using alcoholic alkali at room temperature, to give the dicarboxylic acid products of this invention (formula I).

The compounds of this invention are described herein as racemates or diastereoisomers. These mixtures may be resolved into individual d- and l- optical isomers, such as those due to the assymetric carbon ring member at the 3-position, by using methods known to the art, for example, by forming salts with optically pure bases. Also, during the Diels-Alder step of the reaction sequence, theoretically both the exo and endo forms of the bicyclo[2.2.1]heptene may be formed. In fact, we have isolated only the exo forms. The endo forms are prepared from the exo isomers of formula I as known to the art.

The nomenclature of the bicyclo[2.2.1]heptanes employed herein treats the compounds as substituted heterocyclic compounds. They may equally well be named as 2-azabicyclo[2.2.1]heptane-3-carboxylic acids or derivatives thereof.

The following examples are designed to illustrate the preparation of the new chemical compounds of this invention. Temperatures are in degrees Centigrade. Other variations of these examples will be obvious to those skilled in the art.

EXAMPLE 1

Benzyl carbamate (137 g, 0.91 m) was added to a stirred mixture of 96 g (1.09 m) of freshly distilled methyl glyoxylate and 1.2 l of anhydrous ether. The mixture was reduced in volume by evaporating 300 ml of ether which was then replaced with 300 ml of dry acetone. The mixture was heated at reflux for 24 hours. After cooling in ice, the mixture was concentrated to 700 ml. Chilling gave 90.0 g, mp 101°–103°, of crystalline benzyl N-carbomethoxy-2-hydroxyglycinate. The product was recrystallized from toluene for analysis.

Anal. Calcd. for $C_{11}H_{13}NO_5$: C, 55.23; H, 5.48; N, 5.86. Found: C, 55.28; H, 5.51; N, 5.78.

A mixture of 40.62 g (0.178 m) of the hydroxyglycinate, 13 ml (0.178 m) of thionyl chloride, 0.4 ml of pyridine and 200 ml of methylene chloride was heated at reflux for 1 hour. The mixture was cooled, filtered and evaporated under reduced pressure. The residue was mixed with 21.8 g (0.215 m) of triethylamine and, then, with 24 g (0.363 m) of cyclopentadiene in methylene chloride at 0°. The mixture was stirred at room temperature for 18 hours. After working up, the product isolated was 40 g (78%) of crude 2-carbobenzyloxy-3-carbomethoxy-2-azabicyclo[2.2.1]hept-5-ene.

The product was purified over a silica gel column using 2:1 petroleum ether/ethyl acetate to give 31.35 g of purified product, mp 170°, mE=287.

The heptene ester (9.08 g, 0.0316 m) was dissolved in 150 ml of ethyl acetate. After 900 mg of 10% palladiumon-charcoal had been added, the mixture was hydrogenated on a Parr shaker for 20 hours. The catalyst was removed. The filtrate was evaporated under reduced pressure to give 4.79 g (98%) of syrupy base which was taken up in 100 ml of ethyl ether, then, made acid with hydrogen chloride to separate 5.37 g (88%) of 3-carbomethoxy-2-azabicyclo[2.2.1]heptane hydrochloride, mp 163°–165°.

Anal. Calcd. for $C_8H_{13}NO_2 \cdot HCl$: C, 50.14; H, 7.36; N, 7.31. Found: C, 50.06; H, 7.70; N, 7.29.

The hydrochloride (500 mg) is covered with bicarbonate/ethyl acetate. After shaking, the organic layer is separated, washed and evaporated to leave the free base, 3-carbomethoxy-2-azabicyclo[2.2.1]heptane.

The bicycloheptane hydrochloride (3.83 g, 0.02 m) was mixed with 4.55 g (0.045 m) of triethylamine and 70 ml of dry acetone. After stirring the mixture at 0° for a few minutes, a solution of 3.29 g (2.76 m) of 4-carbomethoxybutanoyl chloride in 10 ml of acetone was added slowly. The suspension was stirred at room temperature overnight. The triethylamine hydrochloride was separated by filtration and washed with acetone. The organic extracts and mother liquors were combined and evaporated under reduced pressure to give a syrupy product which was dissolved in 50 ml of ethyl acetate. After washing with 2N hydrochloric acid, water, bicarbonate, water and brine, the organic extract was evaporated to give 2.65 g (47%) of bis ester product.

This material (2.46, 0.0086 m) was dissolved in 20 ml of 1:1 methanol/water and 1.09 g (0.019 m) of potassium hydroxide added. After standing at room temperature overnight, the mixture was concentrated to 10 ml and taken over a 10 g column of a polystyrene sulfonic acid resin (Dowex 50-X8). After elution with water, 2.35 g of syrup remained which was dissolved in acetonitrile, then, reacted with 3.7 ml of dicyclohexylamine. After cooling, the solvent was decanted. The residue was triturated with acetonitrile to give 3.19 g of 2-carboxy-3-(4-carboxybutanoyl)-3-azabicyclo[2.2.1]heptane, dicyclohexylamine salt, mp 155°–159°, after recrystallization from tetrahydrofuran-acetonitrile.

Anal. Calcd. for $C_{12}H_{17}NO_5 \cdot C_{12}H_{23}N$: C, 66.03; H, 9.23; N, 6.42. Found: C, 68.34, 68.59; H, 9.86, 9.85; N, 6.64, 6.30.

The salt was dissolved in 10 ml of water. The mixture was made basic with sodium hydroxide, washed with ether and chromatographed over acid resin as described above to give 1.05 g (47%) of amorphous product as the free dicarboxylic acid.

Anal. Calcd. for $C_{12}H_{17}NO_5 \cdot 0.5\ H_2O$: C, 54.55; H, 6.86; N, 5.30. Found: C, 54.44; H, 6.70; N, 5.22.

This N-glutaryl compound did not demonstrate renal vasodilator activity within the time of the test protocol for renal activity at 3, 30 or 300 μg/kg/min infusion in three anesthetized dogs in the protocol described in U.S. Pat. No. 4,197,297. When the compound was administered initially to two dogs at 300 mg/kg/min, renal blood flow (RBF) increased 77%, renal vascular resistance (RVR) decreased 44% and heart rate (HR) decreased 11%, demonstrating an accumulative kidney function improvement. At 25 and 50 mg/kg i.p., the N-glutaryl congener increased urine and ion output in the spontaneously hypertensive rat (SHR) test, demonstrating diuretic activity.

The glutaryl congener (200 mg) is mixed with 100 mg of lactose, filled into a hard gelatin capsule and administered orally from 3–6 times daily to a patient in need of improvement of kidney function.

EXAMPLE 2

A mixture of 1.0 g (0.005 m) of 3-carbomethoxy-2-azabicyclo[2.2.1]heptane hydrochloride from Example 1 and 20 ml of 6N hydrochloric acid was heated on a steam bath for 18 hours. The mixture was evaporated to dryness under reduced pressure. The last amount of water was azeotroped off with ethanol-toluene. The residue was triturated with acetone to give a white crystalline solid, 0.86 g (92%), mp 185°–189°, of 3-carboxy-2-azabicyclo[2.2.1]heptane hydrochloride. A sample was further purified from isopropanol-acetone, m.p. 191°–193°.

Anal. Calcd. for $C_7H_{11}NO_2 \cdot HCl$: C, 47.33; H, 6.81; N, 7.89. Found: C, 47.59; H, 6.85; N, 8.00.

The free base is obtained by titrating the hydrochloride salt with an alcoholic solution of sodium hydroxide. The amino acid is then N-acylated with a half ester half acid chloride under Schotten-Baumann conditions to give the desired compound of this invention. The alkali metal salts of the amino acid are also easily prepared. For example, 250 mg of the parent compound is reacted with an excess of sodium 2-ethylhexanoate in acetone to prepare the sodium salt.

EXAMPLE 3

Using the method of Example 1, 4.45 g (0.0232 m) of 3-carbomethoxy-2-azabicyclo[2.2.1]heptane hydrochloride and 3-carbethoxypropanoyl chloride were reacted using triethylamine and acetone to give 4.59 g of syrupy 2-(3-carbethoxypropanoyl)-3-carbomethoxy-2-azabicyclo[2.2.1]heptane.

This compound (4.43 g, 0.0156 m) was saponified using 2.63 g of potassium hydroxide in 100 ml of 1:1 water/methanol at room temperature for 18 hours to give 2-(3-carboxypropanoyl)-3-carboxy-2-azabicyclo[2.2.1]heptane as the diacid, mp 132°–135°.

Anal. Calcd. for $C_{11}H_{15}NO_5$: C, 54.77; H, 6.27; N, 5.81. Found: C, 54.84; H, 6.45; N, 5.66.

This compound did not increase renal blood flow or decrease renal vascular resistance within the protocol time of the anesthetized dog test at infusion rates of from 3–300 μg/kg/min. It is predicted to have utility for improving kidney function on an accumulative basis as does the product of Example 1.

This N-succinyl compound in ethyl acetate is reacted with an excess of sodium 2-ethylhexanoate in acetone/isopropanol to form the disodium salt.

EXAMPLE 4

A mixture of 3.83 g (0.02 m) of 3-carbomethoxy-2-azabicyclo[2.2.1]heptane hydrochloride from Example 1, 3.29 g (0.02 m) of 4-carbomethoxy-2-methylbutanoic acid, 2.3 g of N-ethylmorpholine, 5.4 g of 1-hydroxybenzotriazole, 4.13 g of dicyclohexylcarbodiimide and 60 ml of dry tetrahydrofuran was prepared with cooling and stirring, then, allowed to stir at room temperature for 18 hours. The mixture was filtered. The filtrate was evaporated to give a syrup which was dissolved in ethyl acetate and washed with 10% acetic acid/water and water. A solid separated. The ethyl acetate extract was further washed with 5% sodium bicarbonate solution and brine, then, dried and evaporated under reduced pressure to give 3.41 g (57%) of 3-carbomethoxy-2-(4-carbomethoxy-2-methylbutanoyl)-2-azabicyclo[2.2.1]heptane, mE 297.

This ester (3.29 g, 0.011 m) with 1.7 g (0.3 m) of potassium hydroxide and 30 ml of 1:1 methanol/water was stirred at room temperature for 18 hours. The mixture was concentrated to 10 ml volume, diluted with 20 ml of water, washed with ether, then, reconcentrated.

The product was taken over a styrene sulfonic acid resin column as described above to give 2.8 g of resinous 3-carboxy-2-(4-carboxy-2-methylbutanoyl)-2-azabicyclo[2.2.1]heptane hydrate, mE 270 (MH⊕).

Anal. Calcd. for $C_{13}H_{19}NO_5$: C, 57.22; H, 7.16; N, 5.13. Found: C, 57.35; H, 7.26; N, 4.79.

This acid was dissolved in acetonitrile and reacted with 4.17 ml of dicyclohexylamine to give a non-crystalline salt from which the acid was regenerated using the column resin purification described above.

This dicarboxylic acid at 3 μg/kg/min in 2 anesthetized dogs increased renal blood flow 15.5% and reduced renal vascular resistance 12.5%. Significant activity was not demonstrated at 30 and 300 μg/kg/min within the time of the protocol. At 50 mg/kg, intraperitoneally, in spontaneously hypertensive rats this compound demonstrated a significant increase in excretion of urine. An increase of sodium and potassium excretion was not observed at this dose.

EXAMPLE 5

Substituting ethyl glyoxate in the method of Example 1 gives, in succession, benzyl N-carbethoxy-2-hydroxyglycinate, 2-carbobenzyloxy-3-carbethoxy-2-azabicyclo[2.2.1]hept-5-ene, 3-carbethoxy-2-azabicyclo[2.2.1]heptane and 3-carboxy-2-(4-carboxybutanoyl)-2-azabicyclo[2.2.1]heptane, the same end product as in Example 1. Substituting benzyl glyoxate gives benzyl N-carbobenzyloxy-2-hydroxyglycinate, 2,3-dicarbobenzyloxy-2-azabicyclo[2.2.1]hept-5-ene, after catalytic hydrogenation, 3-carboxy-2-azabicyclo[2.2.1]heptane and the same end product as in Example 1.

What is claimed is:
1. A compound of the formula:

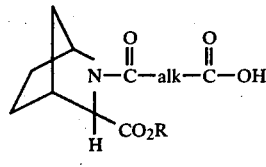

in which:
R is hydrogen, lower alkyl of 1–5 carbons or benzyl; and
alk is an alkylene chain of 2–5 carbons separating the carboxy and carboxamido groups to which it is attached by at least 2 carbons; or a pharmaceutically acceptable alkali metal or organic amine salt thereof.

2. The compound of claim 1 in which the $C_3$–$C_5$ alkylene chain separates the carboxy and carboxamido groups by at least 3 carbons.

3. The compound of claim 1 in which R is hydrogen.

4. The compound of claim 1 being 3-carboxy-2-(4-carboxybutanoyl)-2-azabicyclo[2.2.1]heptane.

5. The compound of claim 1 being 3-carboxy-2-(4-carboxy-2-methylbutanoyl)-2-azabicyclo[2.2.1]heptane.

6. A compound of the formula:

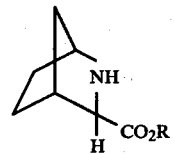

in which R is hydrogen, benzyl or lower alkyl; and its acid addition salts, or, when R is hydrogen, alkali metal or organic amine salts suitable for chemical intermediate use.

7. The compound of claim 6 being 3-carboxy-2-azabicyclo[2.2.1]heptane.

8. The compound of claim 6 being 3-carbomethoxy-2-azabicyclo[2.2.1]heptane.

9. The compound of claim 6 being 3-carboethoxy-2-azabicyclo[2.2.1]heptane.

10. The compound of claim 6 being 3-carbomethoxy-2-azabicyclo[2.2.1]heptane hydrochloride.

* * * * *